United States Patent
Ferrandis et al.

(10) Patent No.: US 7,897,578 B2
(45) Date of Patent: Mar. 1, 2011

(54) PEPTIDES WITH ANTI-PROLIFERATIVE ACTIVITY

(75) Inventors: Eric Ferrandis, Saint Remy les Chevreuse (FR); José-Antonio Camara Y Ferrer, Paris (FR); Jean-Grégoire Marin, Palaiseau (FR)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 10 days.

(21) Appl. No.: 12/304,746

(22) PCT Filed: Jun. 11, 2007

(86) PCT No.: PCT/FR2007/000955

§ 371 (c)(1),
(2), (4) Date: Dec. 12, 2008

(87) PCT Pub. No.: WO2007/144492

PCT Pub. Date: Dec. 21, 2007

(65) Prior Publication Data

US 2009/0209466 A1     Aug. 20, 2009

(30) Foreign Application Priority Data

Jun. 12, 2006 (FR) .................................. 06 05193

(51) Int. Cl.
*A61K 38/00* (2006.01)
(52) U.S. Cl. .................................................... 514/21.4
(58) Field of Classification Search ........................ None
See application file for complete search history.

(56) References Cited

FOREIGN PATENT DOCUMENTS

| WO | WO 98/23741 A1 | 6/1998 |
| WO | WO 98/58059 | * 6/1998 |
| WO | WO 2005/103079 A1 | 11/2005 |

OTHER PUBLICATIONS

Bork et al., Go hunting in sequence databases but watch out for the traps, 1996, Trends in Genetics, vol. 12, pp. 425-427.*
Bork, Powers and Pitfalls in Sequence Analysis: the 70% hurdle, 2000, Genome Research, vol. 10, pp. 398-400.*
Brenner, Errors in genome annotation, 1999, Trends in Genetics, vol. 15, pp. 132-132.*
Doerks et al., Protein annotation: detective work for function prediction, 1998, Trends in Genetics, vol. 14, pp. 248-250.*
Skolnick et al., From genes to protein structure and function: novel applications of computational approaches in the genomic era, 2000, Trends in Biotech, vol. 18, Issue 1, pp. 34-39.*
Smith et al., The challenge of genome sequence annotation or "the devil is in the details", 1997, Nature Biotechnology, vol. 15, pp. 1222-1223.*
International Search Report (Form PCT/ISA/210) in PCT/FR2007/000955.
Written Opinion (Form PCT/ISA/237) in PCT/FR2007/000955.
Ido, et al. "Prevention of vascular and neural dysfunction in diabetic rats by C-peptide," *Science* vol. 277, pp. 563-566 (Jul. 25, 1997).
Songok, et al. "Identification of env CRF-10 among HIV Variants Circulating in Rural Western Kenya," AIDS Research and Human Retroviruses, vol. 19, No. 2, pp. 161-165 (2003).

* cited by examiner

*Primary Examiner*—Robert Landsman
*Assistant Examiner*—Ian Dang
(74) *Attorney, Agent, or Firm*—Hunton & Williams LLP

(57) ABSTRACT

The present invention relates to peptides with anti-proliferative activity, of sequence SEQ ID No. 1, SEQ ID No. 2 or SEQ ID No. 3.

17 Claims, 3 Drawing Sheets

Days

Legend:
- ▽ Vehicle
- ● Without treatment
- ■ Compound 1 (10 mg/kg)
- ◆ Compound 1 (5 mg/kg)

PEPTIDES WITH ANTI-PROLIFERATIVE ACTIVITY

CROSS-REFERENCE TO RELATED APPLICATIONS

This application is the U.S. National Phase Application of International Application No. PCT/FR2007/000955, filed Jun. 11, 2007, which claims the benefit of French Application No. FR 0605193, filed Jun. 12, 2006, the disclosures of each of which is hereby incorporated by reference.

FIELD OF THE INVENTION

A subject of the present invention is polypeptides and peptides with anti-proliferative activity or one of their pharmaceutically acceptable salts, as well as their use for the prevention or treatment of cancer.

BACKGROUND

Numerous types of cancer exist. Among these there can be mentioned in particular neuroblastoma.

Neuroblastoma is a relatively rare cancer of the sympathetic nervous system which mainly affects children. Neuroblastoma is a malignant tumour which is most common in children, developing from progenitor cells of the neural crest having to colonize the adrenal medulla and the sympathetic ganglions. Neuroblastoma is usually found in babies and young children. Approximately 96% of cases of neuroblastomas appear before the age of 10 years. The disease generally appears in the adrenal medulla gland or in other sites of the sympathetic nervous tissue, the most common site being in the abdomen in the vicinity of the adrenal gland. Neuroblastomas can also be found in the chest, neck or pelvis. Patients suffering from a neuroblastoma type cancer have a high probability of detection. Frequent symptoms of neuroblastomas are pressure caused by the tumour or bone pain. Neuroblastomas can also compress the spinal cord causing paralysis. Cases of fevers, anaemia, or high blood pressure can also be noted.

The treatment of neuroblastoma is based on a multidisciplinary approach essentially combining surgery, radiotherapy and chemotherapy. Among the treatments known at present, the treatments using cyclophosphamide, doxorubicin, etoposide, platinum salts or vincristine can be mentioned.

Among the cancers, leukaemias can also be mentioned.

The term leukaemia refers to a set of cancers affecting the blood. The average adult possesses approximately five liters of blood, the role of which is to provide nutritive elements, oxygenation and the evacuation of waste. Blood is composed of erythrocytes, leukocytes, platelets and plasma. Leukocytes aid in combating infection. Blood platelets form clots preventing the loss of blood during injuries and haemorrhages. Approximately 55% of the blood is constituted by plasma, a light straw coloured liquid which contains the blood cells and the platelets, and transports the food originating from digestion and the hormones originating from the glands into the organism. As indicated, the leukocytes are responsible for a defence mechanism. There are two main types of leukocytes, the lymphocytes and the monocytes. There are two types of lymphocytes, the B lymphocytes, involved in the production of antibodies, and the T lymphocytes. The T lymphocytes are also divided into 3 groups: the inflammatory T cells, which recruit macrophages and neutrophils at the site of the infection or any other damaged tissue; the cytotoxic T lymphocytes, which kill the viruses which have infected cells; and T-helper cells, which increase the production of the antibodies by the B cells. Acute lymphoblastic leukaemia is the most common leukaemia in children. This is a cancer of the leukocytes, specifically of the lymphocytes. The cancerous leukaemia cells are blood cells which no longer function normally. As a result, the leukocytes cannot help the body to combat infections. For this reason, children with an acute lymphoblastic leukaemia frequently have infections and have fevers. Depending on the number of abnormal cells and their location, patients with leukaemia can have a certain number of symptoms. Children with acute lymphoblastic leukaemia frequently have small quantities of erythrocytes and healthy platelets. As a consequence, there are not enough erythrocytes to carry oxygen to the organs, which results in anaemia, with patients possibly seeming pale with a sensation of weakness and fatigue. When there are not enough platelets, patients bleed and are easily injured. Certain common symptoms of acute lymphoblastic leukaemia include: fever; fatigue; frequent infections; pallor; easy bleeding or bruising; small reds spots (called petechiae) under the skin; and/or pain in the bones or joints.

Leukaemia treatments known at present are inter alia the treatments using Ara-C, Idarubicin, Daunorubicin, Melphalan or Busulphan.

Among the cancers, prostate cancers can also be mentioned.

Prostate cancer is a common cancer exclusively affecting men. The prostate forms part of the male reproductive system. A healthy prostate is the size of a chestnut. The prostate is an organ situated immediately below the bladder, behind the symphysis pubis and in front of the rectum. It surrounds the ureter, the duct evacuating urine, over 3 to 4 cm. The prostate is a gland which produces part of the seminal liquid. An enlarged prostate will squeeze the ureter posing urinary problems by slowing down or stopping the flow of the urine from the bladder to the penis. More than 70% of all prostate cancers are diagnosed in men generally above the age of 65 years. Although the etiology of prostate cancer is unknown, the risk factors include the environment, genetics and family history. The mortality rate for prostate cancer is at least twice as high in Afro-American men as in Caucasian men. Because of the additional risk, earlier screening for prostate cancer is recommended for Afro-American men. According to the American Cancer Society, men aged 50 years and more, and those above the age of 45 years who are in the high-risk groups, such as Afro-American men and men with a family history of prostate cancer, should have a blood analysis to screen for the prostate specific antigen (PSA) and a rectal examination each year. The symptoms of prostate cancer generally include: urinary problems; an inability to urinate, or difficulty in starting or stopping the flow of urine; the need to urinate frequently, particularly at night; a weak or interrupted flow of urine; pain or burning during micturition; difficulty in achieving an erection; the presence of blood in the urine or sperm; and frequent pain in the lower back, hips or thighs.

The treatments known at present for treating prostate cancer are inter alia the use of a peptide, triptorelin, which is an analogue of the LHRH (Luteinizing Hormone Releasing Hormone), used to the extent that the growth of tumour cells is under androgenic hormonal control. Very frequently, after a long period of treatment with LHRH analogues, the tumour cells lose their sensitivity to hormonal control and then become hormone-resistant.

Chemotherapy is preferably used in prostate cancer when the latter has developed with an extraprostatic extension and it no longer responds to hormonal treatment. It comprises the use of products or mixtures of products such as docetaxel, paclitaxel, estramustine/docetaxel, estramustine/etoposide, estramustine/vinblastine, and estramustine/paclitaxel.

The treatment of cancers, such as for example neuroblastoma, leukaemia, prostate cancer, breast cancer, melanoma or colorectal cancer can be local or systemic. The local treatments, such as surgery and radiation, affect the cancerous cells of the tumour and the sector close to the latter. The systemic treatments, such as chemotherapy, hormonal therapy, and biological therapy, are conveyed by the blood circulation, reaching cancerous cells everywhere in the body, but also healthy cells causing many undesirable effects.

SUMMARY OF INVENTION

In order to meet industrial requirements, it has become necessary to find new cancer treatments and in particular other compounds having an anti-cancer activity.

Also the problem that the invention is proposed to solve is to provide new compounds having an anti-cancer activity.

Unexpectedly, the inventors have demonstrated that peptides of sequence SEQ ID No. 1 or SEQ ID No. 2 or SEQ ID No. 3 possess an anti-proliferative activity.

To this end the present invention proposes a polypeptide with at most 150 amino acids comprising at least one peptide sequence chosen from the sequence SEQ ID No. 1 or SEQ ID No. 2 or SEQ ID No. 3.

The invention also proposes as a medicament, the peptide of sequence SEQ ID No. 1 or SEQ ID No. 2 or SEQ ID No. 3, as well as the polypeptide described above.

The invention also relates to pharmaceutical compositions comprising the polypeptide or peptide according to the invention.

Finally, a subject of the invention is also the use of the polypeptides, peptides and compounds according to the invention for treating or preventing cancers of the colon, rectum, breast, lungs, pancreas, testicles, kidney, uterus, ovary, prostate, skin, bones, and spinal cord as well as sarcomas, carcinomas, fibroadenomas, neuroblastomas, leukaemias, lymphomas, and melanomas.

The invention also relates to antibodies directed against the polypeptides, peptides or compounds according to the invention.

DETAILED DESCRIPTION

Figure 1:
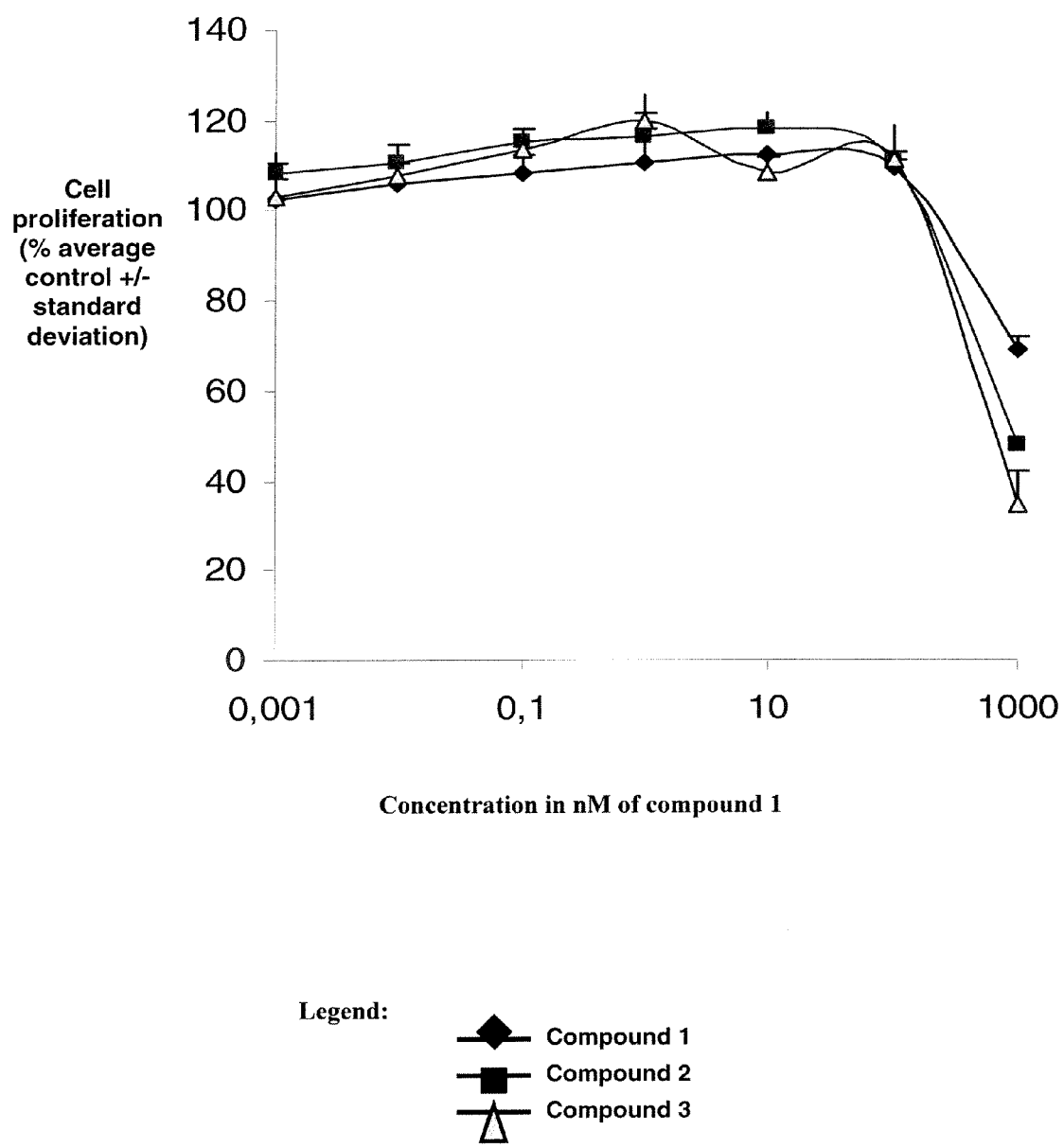
FIG. 1 illustrates the effects of compounds 1, 2, and 3 on the proliferation of tumor cells of human SHSY-5Y neuroblastomas.

The invention offers determinate advantages, in particular the polypeptides, peptides or compounds according to the invention being very specific to the targeted cells, which reduces side effects.

Advantageously, the polypeptides, peptides or compounds according to the invention or their salts have increased solubility in biological media, in particular in aqueous media.

An advantage of the invention is that it can be implemented in all industries, in particular the pharmaceutical, veterinary or cosmetic industry.

Other advantages and characteristics of the invention will become clearly apparent on reading the following description and examples which are given purely by way of illustration and are not limitative.

By the expression cancer, is meant within the meaning of the invention any type of cancer, i.e. invasive, non-invasive, infiltrating, hormonal, non-hormonal, localized or metastatic.

By the expression polypeptide, is meant within the meaning of the invention a macromolecule comprising at least 31 amino acid residues. These amino acids form or do not form a continuous, linear or non-linear, branched or non-branched sequence. A polypeptide according to the invention can also comprise variant polypeptides as defined hereafter.

By the expression peptide, is meant within the meaning of the invention an amino acid sequence comprising at most 30 amino acid residues. These amino acids form or do not form a continuous, linear or non-linear, branched or non-branched sequence. A peptide according to the invention can also comprise variant peptides as defined hereafter.

The invention relates to a polypeptide with at most 150 amino acids comprising at least one peptide sequence chosen from the sequence SEQ ID No. 1, SEQ ID No. 2 or SEQ ID No. 3.

In particular, the invention relates to a polypeptide with at most 100 amino acids comprising at least one peptide sequence chosen from the sequence SEQ ID No. 1, SEQ ID No. 2 or SEQ ID No. 3.

In particular, the invention relates to a polypeptide with at most 75 amino acids comprising at least one peptide sequence chosen from the sequence SEQ ID No. 1, SEQ ID No. 2 or SEQ ID No. 3.

More particularly, the polypeptide according to the invention is a polypeptide with at most 50 amino acids comprising at least one peptide sequence chosen from the sequence SEQ ID No. 1, SEQ ID No. 2 or SEQ ID No. 3.

Still more particularly, the polypeptide according to the invention is a polypeptide with at most 35 amino acids comprising at least one peptide sequence chosen from the sequence SEQ ID No. 1, SEQ ID No. 2 or SEQ ID No. 3.

A subject of the invention is also a peptide with at most 30 amino acids comprising at least one peptide sequence chosen from the sequence SEQ ID No. 1, SEQ ID No. 2 or SEQ ID No. 3.

A subject of the invention is also a peptide with at most 25 amino acids comprising at least one peptide sequence chosen from the sequence SEQ ID No. 2 or SEQ ID No. 3.

More particularly, the peptide according to the invention is a peptide with at most 18 amino acids comprising at least the peptide sequence SEQ ID No. 2 or SEQ ID No. 3.

Still more particularly, the peptide according to the invention is a peptide with at most 10 amino acids comprising at least the peptide sequence SEQ ID No. 3.

A subject of the invention is also a peptide of sequence SEQ ID No. 1 reproduced hereafter:

```
Tyr Thr Val Leu Ser Val Gly Pro Gly Gly Leu Arg

Ser Gly Arg Leu Pro Leu Gln Pro Arg Val Gln Leu

Asp Glu Arg.
```

A subject of the invention is also a peptide of sequence SEQ ID No. 2 reproduced hereafter:

```
Ser Gly Arg Leu Pro Leu Gln Pro Arg Val Gln Leu

Asp Glu Arg.
```

A subject of the invention is also a peptide of sequence SEQ ID No. 3 reproduced hereafter:

Val Gln Leu Asp Glu Arg.

According to a variant of the invention, the polypeptide, peptide or compound according to the invention can have modifications.

According to a variant of the invention, the polypeptide or the peptide according to the invention can be a variant polypeptide or peptide, which signifies a polypeptide or peptide which differs from the native polypeptide or peptide by substitutions, insertions, deletions and/or modifications of amino acids. Certain variants contain conservative substitutions. A conservative substitution is a substitution in which an amino acid is substituted by another amino acid having the same properties, such as those determined by a person skilled in the art who expects no change in the secondary structure, as well as in the hydropathic nature of the polypeptide or peptide. The amino acid substitutions can generally be carried out on the basis of similarity of polarity, charge, solubility, hydrophobicity, hydrophilicity, and/or the amphipathic nature of the residues. For example, negatively charged amino acids include aspartic acid and glutamic acid; positively charged amino acids include lysine and arginine; and non-charged polar amino acids having similar hydrophobicity values include leucine, isoleucine and valine; glycine and alanine; asparagine and glutamine; serine, threonine, phenylalanine and tyrosine. Other groups of amino acids which can represent conservative changes are in particular the following:
group (1) Ala, Pro, Gly, Glu, Asp, Gln, Asn, Ser, Thr;
group (2) Cys, Ser, Tyr, Thr;
group (3) Val, Ile, Leu, Met, Ala, Phe;
group (4) Lys, Arg, His;
and (5) Phe, Tyr, Trp, His.

A variant can also, or alternatively, contain non-conservative changes.

Variants forming part of this invention also include polypeptides or peptides in which the primary structure of the native polypeptide or peptide is modified by insertion of chemical spacers between 2 amino acids.

Variants forming part of this invention also include polypeptides or peptides in which the primary structure of the native polypeptide or peptide is modified by formation of covalent or non-covalent conjugates with other polypeptides or chemical structures such as lipid groups or glycosyl or acetyl phosphate groups.

Variants forming part of this invention also include polypeptides or peptides in which the primary structure of the native polypeptide or peptide is modified by deletion of one or more amino acid residues, the deleted amino acids being able to be contiguous or non-contiguous.

The present invention also includes polypeptides or peptides with or without glycosylation units. For example, the polypeptide or the peptide according to the invention can be glycosylated or comprise glycosylation residues such as acetyls. In this case acetyl groups are grafted onto the peptide chain.

The present invention also includes polypeptides or peptides carrying one or more cleavage site mutations by the proteases allowing resistance to the proteases and therefore increased stability in the circulation.

According to a particular embodiment of the invention, the polypeptide or the peptide according to the invention has arginine residues of the sequences SEQ ID No. 1 or SEQ ID No. 2 or SEQ ID No. 3 which are wholly or partially deleted, modified or replaced by other amino acids.

The polypeptide or peptide according to the invention can also comprise an amide function at one of its ends, or at both its ends.

Preferably, a subject of the invention is a compound of the formula or peptide amide of the sequence SEQ ID No. 1 reproduced hereafter:

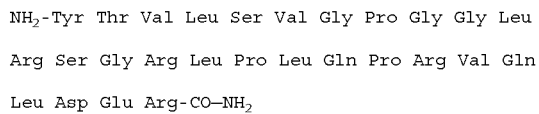

Preferably, a subject of the invention is also a compound of the formula or a peptide amide of the sequence SEQ ID No. 2 reproduced hereafter:

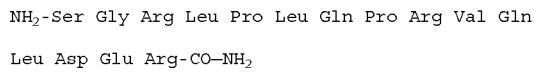

Preferably, a subject of the invention is also a compound of the formula or a peptide amide of the sequence SEQ ID No. 3 reproduced hereafter:

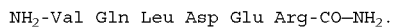

The modifications and variants described above for the polypeptide or peptide according to the invention are also valid for the compound according to the invention.

Preferably, the polypeptide, peptide or compound according to the invention is linear, but it is possible for it to be presented in the circular or helical form.

The polypeptide, peptide or compound according to the invention can comprise levogyral (L) or dextrogyral (D) amino acids or both.

Preferably, the polypeptide, peptide or compound according to the invention comprises levogyral amino acids.

A subject of the invention is also the peptide of sequence SEQ ID No. 1 or SEQ ID No. 2 or SEQ ID No. 3 for use as a medicament.

A subject of the invention is also the polypeptide according to the invention described above for use as a medicament.

A subject of the invention is also a compound according to the invention described above for use as a medicament.

According to certain aspects of the invention, the polypeptides, peptides, compounds, antibodies according to the invention can be incorporated in pharmaceutical compositions. The pharmaceutical compositions comprise one or more of these products and one or more pharmaceutically acceptable excipients (vehicles).

The invention also relates to pharmaceutical compositions comprising at least one polypeptide, peptide or compound according to the invention.

The invention also relates to antibodies directed against the polypeptides, peptides or compounds according to the invention. The antibodies may be contained in serums, these serums being either polyclonal or monoclonal. According to a variant of the invention it may be a matter of a fragment of an antibody, this fragment comprising the antigen-binding site which specifically fixes the polypeptide, peptide or compound as described previously, and in particular a monoclonal antibody, or a fragment of the latter, which specifically fixes the peptide of sequence SEQ. ID. No. 1, No. 2 or No. 3.

The antibodies can be prepared by any technique available to a person skilled in the art (cf. Harlow and Lane, Antibodies. A Laboratory Manual, Cold Spring Harbor Laboratory, 1988). In general, the antibodies can be produced by cell culture techniques including the generation of monoclonal antibodies or via transfections of genes from antibodies into host cells of bacteria or mammals in order to produce recombinant antibodies.

Among other techniques, it is preferred to use those described hereafter. An immunogen containing the polypeptide, peptide or compound according to the invention is injected into a group of mammals (for example mice, rats, rabbits, sheep or goats). In this stage, the polypeptides, peptides or compounds of the present invention can serve as immunogens without modification.

Alternatively, a superior immune response can be induced if the polypeptide, peptide or compound is joined to a transport protein such as bovine serum albumin or keyhole-limpet hemocyanin.

The immunogen is injected into the host animal, preferably according to a predetermined plan, and the animals are bled periodically. Polyclonal antibodies specific to the polypeptide, peptide or compound according to the invention can thus be purified from such antiserums, for example by affinity chromatography using the polypeptide or peptide coupled to a suitable solid support.

According to another aspect of the present invention, the polypeptides, peptides or compounds as well as their variants according to the invention, can be used in the treatment of proliferative diseases.

Thus, the polypeptides, peptides or compounds, as well as their variants according to the invention, can be used in the treatment of cancerous and pre-cancerous cells as well as cancers. In particular, the polypeptides, peptides or compounds can be used to inhibit growth and induce a modulation of cell proliferation in anticancer therapy, such as for example in specific tumours of the breast or prostate.

Such polypeptides, peptides or compounds can also be used for the therapy of numerous carcinomas including melanomas, multiple forms of glioblastomas, carcinomas of the lung as well as colorectal cancers. Agents which activate the expression of such polypeptides, peptides or compounds can also be used within the framework of these therapies.

According to these aspects of the invention, the polypeptides, peptides or compounds, as well as their variants according to the invention, are preferably incorporated in pharmaceutical compositions as described above.

Patients suitable for the therapy are all warm-blooded animals, and preferably human beings. A patient eligible for a therapy according to the invention may or may not be diagnosed as being affected by a cancer. In other words, the pharmaceutical compositions described above can thus be used to inhibit the development of a cancer at different stages of the disease (to prevent the appearance of a cancer or to treat a patient affected by a cancer).

In a particular manner, a subject of the invention is the use of the polypeptide, peptide or compound described above, as well as their variants, for treating or preventing cancers of the colon, rectum, breast, lungs, pancreas, testicles, kidney, uterus, ovary, prostate, skin, bones and spinal cord as well as sarcomas, carcinomas, fibroadenomas, neuroblastomas, leukaemias, lymphomas and melanomas.

The pharmaceutical compositions of the present invention are administered in a manner appropriate to each specific cancer to be treated.

The polypeptide, peptide or compound according to the invention or its salt can be in solid form, for example powders, granules, tablets, gelatin capsules, liposomes or suppositories. Appropriate solid supports can be, for example, calcium phosphate, magnesium stearate, sugars, lactose, dextrin, starch, gelatin, cellulose, methyl cellulose, sodium carboxymethyl cellulose, and polyvinylpyrrolidine.

The polypeptide, peptide or compound according to the invention or its salt used according to the invention can also be presented in liquid form, for example, solutions, emulsions, suspensions or syrups. Appropriate liquid supports can be for example water, organic solvents such as glycerol or glycols, as well as their mixtures, in varying proportions, in water.

The polypeptide, peptide or compound according to the invention or its salt used according to the invention can also be presented in semi-liquid form, for example gels.

The administration of the polypeptide, peptide or compound according to the invention or its salt used according to the invention can be carried out by topical, systemic, oral or parenteral route, by intramuscular, intravenous, sub-cutaneous, intra-peritoneal injection etc. It is also possible to envisage local administration, to a cancerous or suspected cancerous tumour.

The dose of the product according to the present invention, to be provided for the treatment of the abovementioned diseases or disorders, varies depending on the administration method, the age and the body weight of the subject to be treated as well as the state of the latter, and the pharmacological and pharmacodynamic properties of the polypeptides, peptides or compounds according to the invention.

As an indication, the administration dose envisaged for a medicament according to the invention is comprised between 0.1 µg and 1 g/kg depending on the type of active compound used.

FIG. 1 shows the effect of compounds 1, 2 and 3 on the proliferation of tumour cells of human SHSY-5Y neuroblastomas.

Figure 2:
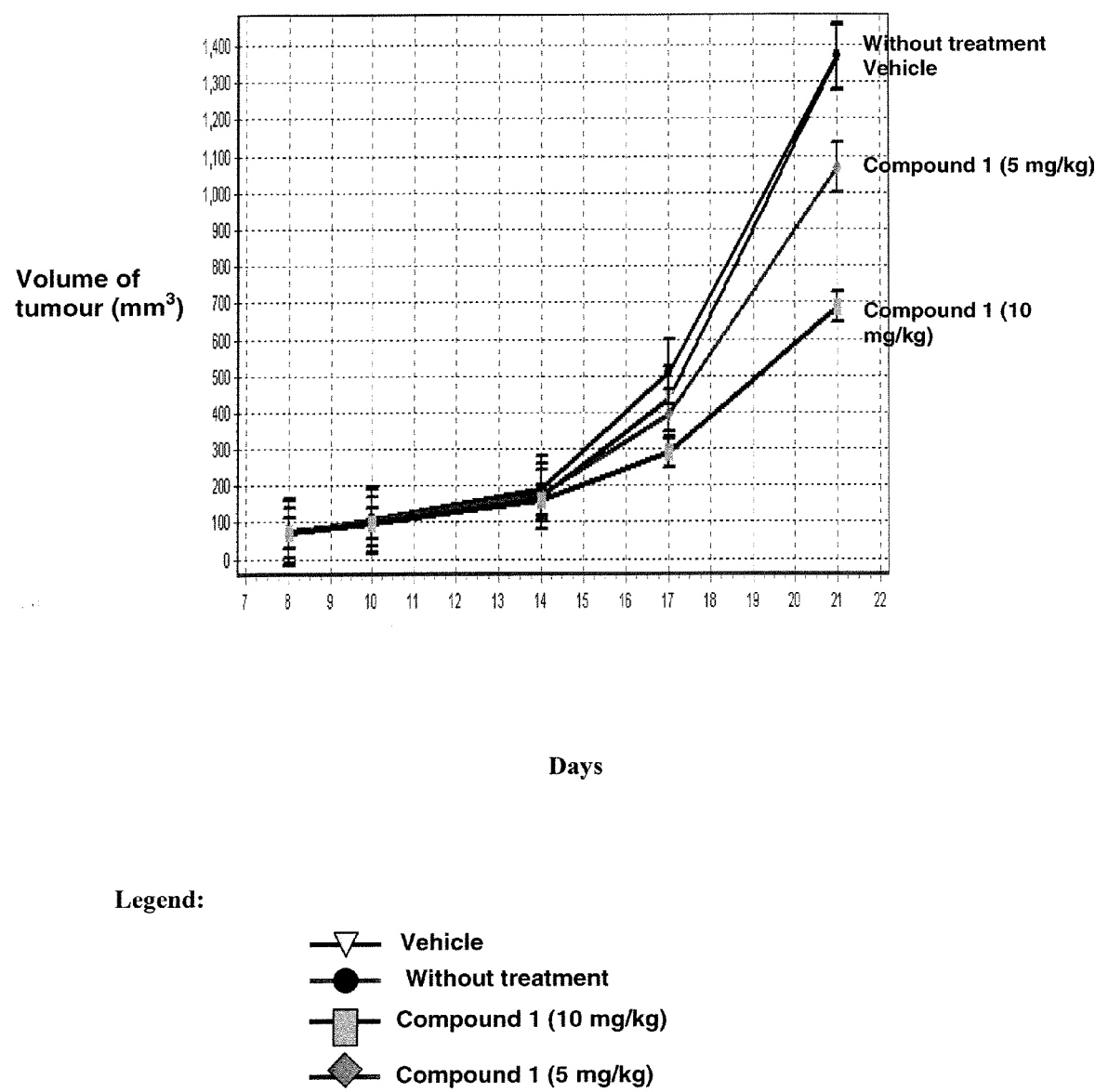
FIG. 2 illustrates the effect of compound 1 on the proliferation of tumor cells of human SHSY-5Y neuroblastomas xenografted into an athymic mouse.

FIG. 2 shows the effect of compound 1 on the proliferation of tumour cells of human SHSY-5Y neuroblastomas xenografted into an athymic mouse.

Figure 3:
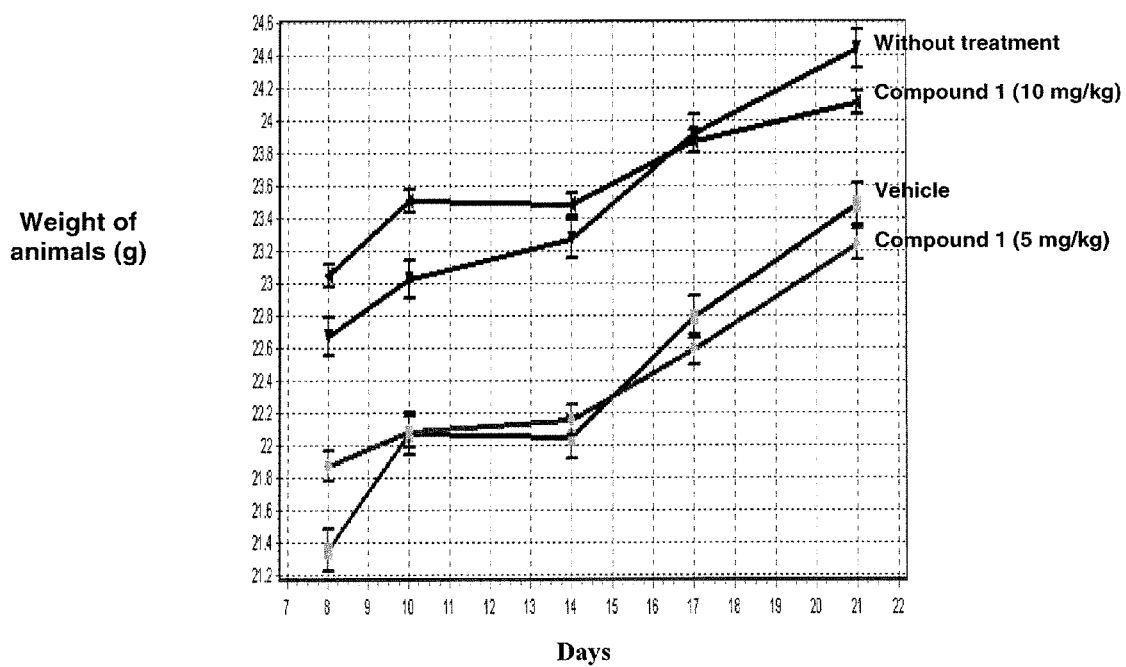
FIG. 3 illustrates the absence of toxicity of compound 1 in a xenografted athymic mouse.

FIG. 3 shows the absence of toxicity of compound 1 in a xenografted athymic mouse.

The following examples illustrate the invention without limiting its scope.

Pharmacological Study of the Products of the Invention

In the examples hereafter:

"Compound 1" designates the compound of the formula or amidated peptide of sequence SEQ ID No. 1 reproduced hereafter:

$NH_2$-Tyr Thr Val Leu Ser Val Gly Pro Gly Gly Leu Arg Ser Gly Arg Leu Pro Leu Gln Pro Arg Val Gln Leu Asp Glu Arg-CO—$NH_2$;

"Compound 2" designates the compound of the formula or an amidated peptide of sequence SEQ ID No. 2 reproduced hereafter:

$NH_2$-Ser Gly Arg Leu Pro Leu Gln Pro Arg Val Gln Leu Asp Glu Arg-CO—$NH_2$;

"Compound 3" designates the compound of the formula or an amidated peptide of sequence SEQ ID No. 3 reproduced hereafter:

$NH_2$-Val Gln Leu Asp Glu Arg-CO—$NH_2$.

1/Synthesis of Compounds 1, 2 and 3:

The synthesis of compounds 1, 2 and 3 was carried out using known peptide synthesis techniques.

The synthesis of compounds 1, 2 and 3 was carried out using so-called F-moc chemistry. The resin used is rink-amide resin, supplied by Applied Biosystems. The amino acids are also obtained from the same supplier. The activation method used is the so-called HAUT/DIPEA method. The cleavage of the resin and lateral protections is carried out by means of the following method: 92% TFA, 4% $H_2O$, 2.5% EDT and 1.5% TIS. The purification is carried out by reversed-phase high pressure liquid chromatography (or HPLC), using aquapore C8 columns, 250×10 mn, 20 μm.

2/In vitro Cell Proliferation Test on Cells of the SHSY-5Y Type with Compounds 1, 2 and 3:

Cancerous cells from human SHSY-5Y neuroblastomas (Code ATCC:CRL-2266) are cultured in DMEM medium (Dulbecco's Modified Eagle's Medium) containing 100 U/ml of penicillin and 100 μg/ml of streptomycin sulphate, complemented with 10% foetal calf serum. The cells are sub-cultured 24 hours before the addition of increasing concentrations of compounds 1, 2 and 3 (0.001/0.01/0.1/1/10/100/1000 nM).

The results are reproduced in FIG. 1, describing the effect of compounds 1, 2 and 3 on the percentage of the number of SHSY-5Y cells.

The 3 compounds show a strong anti-proliferative activity at a dose of 1000 nM on the SHSY-5Y cells.

3/In vivo Cell Proliferation Test on Cells of the SHSY-5Y Type with Compound 1:

Cancerous cells from human SHSY-5Y neuroblastomas (Code ATCC: CRL-2266) are cultured in DMEM medium (Dulbecco's Modified Eagle's Medium) containing 100 U/ml of penicillin and 100 μg/ml of streptomycin sulphate, complemented with 10% foetal calf serum. The cells thus cultured are then xenografted by sub-cutaneous route into the flanks of athymic balb-c NCr-nu/nu mice, aged 4 to 6 weeks.

After a latent period of several days following the graft, the SHSY-SY cells proliferate and form a small tumour (approximately 70 mm$^3$) which is obvious under the flank of the animal.

Compound 1 is, at this stage of growth of the tumour, injected by intra-peritoneal route in doses of 5 and 10 mg/kg.

The results are reproduced in FIG. 2 describing the effect of compound 1 on growth kinetics and tumour volume.

Compound 1 exhibits a dose-dependant anti-tumour activity, linked to its anti-proliferative activity. In fact with the dose of 5 mg/kg, a slowing down of the growth kinetics of the tumour is observed with an approximately 20% reduction in the size of the tumour after 21 days.

This effect is more marked when compound 1 is administered in a dose of 10 mg/kg during which a very clear slowing down of the tumour's growth kinetics is observed, combined with an approximately 50% reduction in the size of the tumour after 21 days.

4/Toxicity Test of Compound 1:

Cancerous cells from human SHSY-5Y neuroblastomas (Code ATCC: CRL-2266) are cultured in DMEM medium (Dulbecco's Modified Eagle's Medium) containing 100 U/ml of penicillin and 100 μg/ml of streptomycin sulphate, complemented with 10% foetal calf serum. The cells thus cultured are then xenografted by sub-cutaneous route into the flanks of athymic mice.

After a latent period of several days, the SHSY-5Y cells proliferate and form a small, obvious tumour (approximately 70 mm$^3$).

Compound 1, at this stage of the tumour's growth, is injected by intra-peritoneal route in doses of 5 and 10 mg/kg.

The results are reproduced in FIG. 3 describing the development of the weight of the animals as a function of time, which is an indicator of the possible toxicity of the products tested in this athymic mouse model.

Compound 1 has no effect on the weight of the animals whatever the tested dose of compound 1 (5 and 10 mg/kg). This result indicates the apparent absence of toxicity of this product.

The invention claimed is:

1. An isolated peptide comprising the amino acid sequence of SEQ ID NO: 1, SEQ ID NO: 2, or SEQ ID NO: 3, wherein said peptide consists of at most 30 amino acid residues.

2. The peptide according to claim 1, wherein the peptide comprises the amino acid sequence of SEQ ID NO: 1.

3. The peptide according to claim 1, wherein the peptide comprises the amino acid sequence of SEQ ID NO: 2.

4. The peptide according to claim 1, wherein the peptide comprises the amino acid sequence of SEQ ID NO: 3.

5. The peptide of claim 1, wherein the peptide is an amide peptide.

6. The peptide of claim 5, wherein the carboxyl terminus of said peptide comprises an amide.

7. An isolated peptide consisting of SEQ ID NO: 1.

8. An isolated peptide consisting of SEQ ID NO: 2.

9. An isolated peptide consisting of SEQ ID NO: 3.

10. A medicament comprising at least one peptide according to claim 1.

11. A medicament comprising the peptide according to claim 7.

12. A medicament comprising the peptide according to claim 8.

13. A medicament comprising the peptide according to claim 9.

14. A pharmaceutical composition comprising at least one peptide according to claim 1.

15. A pharmaceutical composition comprising the peptide according to claim 7.

16. A pharmaceutical composition comprising the peptide according to claim 8.

17. A pharmaceutical composition comprising the peptide according to claim 9.

* * * * *

SEQUENCE LISTING

```
<160> NUMBER OF SEQ ID NOS: 3

<210> SEQ ID NO 1
<211> LENGTH: 27
<212> TYPE: PRT
<213> ORGANISM: Homo sapien

<400> SEQUENCE: 1

Tyr Thr Val Leu Ser Val Gly Pro Gly Gly Leu Arg Ser Gly Arg Leu
1               5                   10                  15

Pro Leu Gln Pro Arg Val Gln Leu Asp Glu Arg
            20                  25

<210> SEQ ID NO 2
<211> LENGTH: 15
<212> TYPE: PRT
<213> ORGANISM: Homo sapiens

<400> SEQUENCE: 2

Ser Gly Arg Leu Pro Leu Gln Pro Arg Val Gln Leu Asp Glu Arg
1               5                   10                  15
```

```
<210> SEQ ID NO 3
<211> LENGTH: 6
<212> TYPE: PRT
<213> ORGANISM: Homo sapiens

<400> SEQUENCE: 3

Val Gln Leu Asp Glu Arg
1               5
```